United States Patent [19]

Gupta

[11] 3,965,191

[45] June 22, 1976

[54] PROCESS FOR SYNTHESIZING METHYL GLYOXAL ACETALS

[75] Inventor: Shyam K. Gupta, Ledyard, Conn.

[73] Assignee: Pfizer Inc., New York, N.Y.

[22] Filed: Mar. 20, 1975

[21] Appl. No.: 560,304

Related U.S. Application Data

[63] Continuation of Ser. No. 422,089, Dec. 5, 1973, abandoned.

[52] U.S. Cl. ................................................ 260/594
[51] Int. Cl.² ........................................ C07C 45/00
[58] Field of Search ................... 260/594, 593 R, 573

[56] References Cited
UNITED STATES PATENTS

| | | | |
|---|---|---|---|
| 2,421,559 | 6/1947 | Guest et al. | 260/594 |
| 3,478,060 | 11/1969 | Maschka et al. | 260/594 |
| 3,607,943 | 9/1971 | Warner | 260/573 R |

*Primary Examiner*—James O. Thomas, Jr.
*Assistant Examiner*—James H. Reamer
*Attorney, Agent, or Firm*—Connolly and Hutz

[57] ABSTRACT

A one-step process for the synthesis of methyl glyoxal acetals from dihydroxyacetone wherein dihydroxyacetone, an alkanol and an acid catalyst are reacted to produce the acetals.

6 Claims, No Drawings

PROCESS FOR SYNTHESIZING METHYL GLYOXAL ACETALS

CROSS-REFERENCE TO RELATED APPLICATION

This application is a continuation of application Ser. No. 422,089 filed Dec. 5, 1973, now abandoned.

BACKGROUND OF THE INVENTION

The preparation of methyl glyoxal acetals by reacting methyl glyoxal with alcohol in the presence of an acid catalyst is disclosed in U.S. Pat. No. 2,421,559. The required starting material for this synthesis, methyl glyoxal, is obtained by oxidation of acetone with selenium dioxide (U.S. Pat. No. 1,955,890), by partial oxidation of propylene glycol (U.S. Pat. No. 2,339,347), or by acid catalyst transformation of dihydroxyacetone (German Pat. No. 1,914,037; Great Britain Pat. No. 1,234,685 and U.S. Pat. No. 3,607,943). Still another process for preparing methyl glyoxal acetals requires the reaction of acetone with an alcohol and a nitrosating agent in the presence of an acid catalyst (U.S. Pat. No. 3,478,060).

U.S. Pat. No. 2,421,559 discloses that the omission of a water-immiscible organic solvent and the use of the monohydric alcohol as the solvent itself results in the formation of large amounts of undesired alkyl esters of an α-alkoxy propionic acid and methyl glyoxal dialkyl acetal dialkyl ketal.

The present one-step process which preferably employs an excess of alkanol surprisingly avoids producing these side or undesirable products. The compounds of the present invention are particularly valuable in the synthesis of growth promotants, for instance, in the synthesis of quinoxaline-di-N-oxide antibacterials.

SUMMARY OF THE INVENTION

The present invention relates to a one-step process for synthesizing methyl glyoxal acetals from dihydroxyacetone wherein dihydroxyacetone is reacted with an alkanol in the presence of catalytic amounts of cation exchange resin produced from the stronger acids having a pK value less than about one. For purposes of the present invention, the pK value is defined as the negative logarithm to the base 10 of the equilibrium constant K determined at 25°C. Mineral acids by themselves can be used as the catalyst, for instance, sulfuric acid. The resultant acetal is then obtained by conventional extraction and distillation procedures. Water is a co-product in this reaction, but its continuous removal is not necessary. Impurities present in the dihydroxyacetone starting material do not interfere with the reaction. The reaction is generally illustrated as follows:

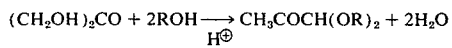

wherein R is alkyl having 1-4 carbon atoms.

As one skilled in the art can readily appreciate, the present process is also operable when an alkanol of up to 10 carbon atoms is employed as a reactant. Similarly, alkanols having as a substitutent a nonreactive moiety are also contemplated in the present invention.

DETAILED DESCRIPTION OF THE INVENTION

The cation exchange resins used in the present process are those based upon the stronger acids as defined above and are generally used in an amount of 1 to 10% by weight of the dihydroxyacetone. Examples of those resins which are suitable for the present invention are sulfonated polystyrene, and sulfonated styrene-divinylbenzene copolymer.

Normally, the reaction is carried out in the absence of a solvent. However, a non-reactive solvent such as benzene, hexane or chloroform can be used.

The alkanol is used in at least an equivalent amount with respect to the dihydroxyacetone (2 mols – 1 mol), however it is preferred to use an excess amount within the range of 2 moles to 200 moles, with a five fold amount particularly preferred (10 mol – 1 mol).

A surprising feature of the invention is that the alkanol can be used in excess amounts to serve as both the reactant and the solvent for the reaction.

A wide range of temperature is possible during the reaction which extends between about 50°–150°C. but preferably is between about 60°–120°C.

The reaction is carried out at either atmospheric, subatmospheric or superatmospheric pressures.

Processing of the resulting reaction mixture is carried out in routine manner by distillation or by extraction of the reaction mixture with a water-immiscible solvent such as methylene chloride after adding water to the reaction mixture.

The acetals of the invention are obtainable in a purity greater than 98% and surprisingly are uncontaminated with any undesirable side products such as 1, 1,2,2-teraalkoxypropane or alkyl α, αdialkoxypropionate as occurs with the prior art practice mentioned above.

The following examples are illustrative of the present invention.

EXAMPLE 1

Methyl Glyoxal Dimethylacetal

A mixture of 90 g of dihydroxyacetone, 270 ml. of methanol and 9 g of a sulfonated polystyrene cationic resin in the acid form is heated at 65° to 70°C. for 16 hrs. The resin catalyst is removed by filtration and the filtrate is diluted with water followed by extraction with methylene chloride. The distillation of methylene chloride extract gave the dimethylacetal in 82% yield of 98% purity.

EXAMPLE 2

The reaction of Example 1 was run at 100°C. in a pressure vessel for 4 hrs. At this point GLPC analysis of the reaction mixture using toluene as an internal standard indicated 96% yield. An 80% isolated yield was achieved upon extraction and distillation as carried out as in Example 1.

EXAMPLE 3

Methyl Glyoxal Di-N-Propylacetal
(1,1-Di-N-propoxy-2-propanone)

A mixture of 36 g of dihydroxyacetone, 200 ml. of 1-propanol, and 4 g of sulfonated polystyrene cationic resin was heated at 80°C. to 90°C. for 5 hrs. The resin catalyst was removed by filtration and the reaction mixture extracted and distilled as described in Example 1 to give the isolated propylacetal product.

EXAMPLE 4

Methyl Glyoxal Di-N-Butyl Acetal
(1,1-Di-N-butoxy-2-propanone)

A mixture of 30 g of dihydroxyacetone, 100 ml. of 1-butanol and 2 g of a sulfonated polystyrene cationic resin was heated at 90°C. to 110°C. for 4 hrs. The resin catalyst was removed by filtration and the filtrate extracted and distilled as described in Example 1 to give the butyl acetal product.

The yields and characterization data of representative examples prepared by this procedure are given in Table I.

Table I

Synthesis of 1,1-Dialkoxy-2-Propanones($H_3C-CO-CH(OR)_2$)

| No. | R Substituent | % Yield GLPC Assay | % Yield Isolated | b.p. | NMR ($CDCl_3$, TMS)δ |
|---|---|---|---|---|---|
| 1. | $CH_3-$ | 96 | 82 | 82°(70 mm) | 2.2 (S, 3H), 2.4 (S, 6H), and 4.43 (S, 1H). |
| 2. | $C_2H_5-$ | 99 | 92 | 82°(50 mm) | 1.23 (T, 6H), 2.2 (S, 3H), 3.7 (M, 4H), 4.53 (S, 1H) |
| 3. | $CH_2CH_2CH_2-$ | 98.5 | 90 | 82°(14 mm) | 0.91 (T, 6H), 1.57 (M, 4H), 2.15 (S, 3H), 3.55 (M, 4H), and 4.5 (S, 1H). |
| 4. |  | 98 | 85 | 59°(14 mm) | 1.1 (pair of doublets, 12H), 2.11 (S, 3H), 3.86 (M, 2H), and 4.55 (S, 14H). |
| 5. | $CH_3CH_2CH_2CH_2-$ | 95 | 90 | 92°(29 mm) | 0.93 (M,) and 1.5 (M, total 14H), 2.15 (S, 3H), 3.61 (M, 4H), and 4.5 (S, 1H). |

What is claimed is:
1. A process for synthesizing a compound having the formula

$CH_3COCH(OR)_2$ wherein R is alkyl having 1–4 carbon atoms, comprising the step of reacting at about 50°–150°C. dihydroxyacetone with at least an equivalent amount of an alkanol having 1–4 carbon atoms in the presence of a catalytic amount of a cation exchange resin produced from an acid having a pK value of less than one.

2. The process of claim 1 wherein the cation exchange resin is a member selected from the group consisting of sulfonated polystyrene and sulfonated styrene-divinylbenzene copolymers.

3. The process of claim 1 wherein the temperature is maintained at about 60°–120°C. during the reaction.

4. The process of claim 1 wherein the catalyst is used in an amount of 1–10% by weight of the dihydroxyacetone.

5. The process of claim 1 wherein the alkanol is used in an excess amount over the equivalent amount within a range of 2–200 mols.

6. The process of claim 1 wherein 10 mols of the alkanol are used per 1 mol of dihydroxyacetone.

* * * * *